(12) United States Patent
Arellano (10) Patent No.: US 7,250,180 B2
(45) Date of Patent: Jul. 31, 2007

(54) ANTI-PROSTATE CANCER COMPOSITION AND THERAPEUTIC USES THEREFOR

(76) Inventor: Edwin Cevallos Arellano, Thomas Chariove 135 y Agustin Zambrano Lace Building, 3rd Floor, Quito (EC)

( * ) Notice: Subject to any disclaimer, the term of this patent is extended or adjusted under 35 U.S.C. 154(b) by 0 days.

(21) Appl. No.: 10/754,077

(22) Filed: Jan. 7, 2004

(65) Prior Publication Data

US 2005/0147701 A1 Jul. 7, 2005

(51) Int. Cl.
*A61K 36/00* (2006.01)
(52) U.S. Cl. .................................. 424/725
(58) Field of Classification Search ............... 424/725, 424/773
See application file for complete search history.

(56) References Cited

U.S. PATENT DOCUMENTS

| 4,698,360 | A | 10/1987 | Masquelier |
| 6,284,289 | B1 | 9/2001 | Van den Berghe |
| 6,514,538 | B1 | 2/2003 | Ota et al. |
| 2002/0086894 | A1* | 7/2002 | Kindness et al. |

OTHER PUBLICATIONS

Milot; HerbClip—www.physiologics.com/herbclip/review.asp?I=43917; 2004.*
BIRM website (www.birm.com/shop/articles.htm—The Most Important Asset Now!—2002).*
Cevallos (BIRM Carbohydrate of low molecular weight ECA 10-142 controls AIDS (1994) Tenth International Conference on Aids (Yokohama, Japan) Abstracts, vol. 2 (abstract No. 0291)).*
Jacobson, Judith S., et al., "Complementary and Alternative Medicine in Prostate Cancer", *Curr Oncol Rep*, (2001),3:448-42.
Jones, Heather A., et al., "Rates of Unconventional Medical Therapy use in Patients with Prostate Cancer: Standard History Versus Directed Questions", *Urology*, (2002),59:272-276.
Kaighn, M. E., et al., "Establishment and Characterization of a Human Prostatic Carcinoma Cell Line (PC-3)", *Investigative Urology*, (1979),17:16-23.
Wang, Min , et al., "Isolation and Characterization of PC-3 human prostatic tumor sublines which preferentially metastasize to select organs in S.C.I.D. mice", *Differentiation*, (1991),48:115-125.
Wenger, Allen S., et al., "In Vitro Characterization of MAT LyLu: A Dunning Rat Prostate Adenocarcinoma Tumor Subline", *The Journal of Urology*, (1984),131:1232-1236.
Lokeshwar, Bal L., et al., "Inhibition of Cell Proliferation, Invasion, Tumor Growth and Metastasis by an Oral Non-Antimicrobial Tetracycline Analog (col. 3) in a Metastatic Prostate Cancer Model", *International Journal of Cancer*, (2002),98:297-309.
Dudak, Scott D., et al., "Enhancement of Radiation Response of Prostatic Carcinoma by Lonidamine", *Anticancer Research*, (1996),16:3665-3671.
Yamamura, Yasuhiro , et al., "A New Flow Cytometric Method for Quantitative Assessment of Lymphocyte Mitogenic Potentials", *Cellular and Molecular Biology*, (1995),41:121-132.
Lokeshwar, Vinata B., et al., "Association of Elevated Levels of Hyaluronidase, a Matrix-degrading Enzyme, with Prostate Cancer Progression", *Cancer Research*, (1996),56:651-657.
Block, Norman L., et al., "Stromal and Epithelial Expression of TUmor Markers Hyaluroinic Acid and HYAL1 Hyaluronidase in Prostate Cancer", *The Journal of Biological Chemistry*, (2001),276:11922-11932.
Lokeshwar, Vinata B., et al., "Identificatin of Bladder Tumor-derived Hyaluronidase: Its SImilarity to HYAL1", *Cancer Research*, (1999),59:4464-4470.
Bitter, Thomas , et al., "Mucopolysaccharides of Whole Human Spleens in Generalized Amyloidosis", *Journal of Clinical Investigation*, (1966),45:963-975.
Harris, Katherine A., et al., "Treatment Options in Hormone-Refractory Prostate Cancer Current and Future Approaches", *Drug*, (2001),61:2177-2192.
Kojima, Munekado , et al., "Use of Prostate-Specific Antigen and Tumor Volume in Predicting Needle Biopsy Grading Error", *Urology*, (1995),45:807-812.
Mans, Dennis R., et al., "Anti-Cancer Drug Discovery and Development in Brazil: Targeted Plant Collection as a Rational Strategy to Acquire Candidate Anti-Cancer Compounds", *The Oncologist*. (2000),5:185-198.
Pienta, Kenneth J., et al., "Effect of Estramustine, Etoposide, and Taxol on Prostate Cancer Cell Growth In Vitro and In Vivo", *Urology*, (1996),48:164-170.
Lokeshwar, Balakrishna L., et al., "Secretion of Matrix Metalloproteinases and Their Inhibitors (Tissue Inhibitor of Metalloproteinases) by Human Prostate in Explant Cultures: Reduced Tissue Inhibitor of Metalloproteinase Secretion", *Cancer Research*, (1993),53:4493-4498.

(Continued)

*Primary Examiner*—Susan Hoffman
(74) *Attorney, Agent, or Firm*—Fox Rothschild LLP; Gerard P. Norton; Shahnam Sharareh (57) ABSTRACT

Disclosed are methods and compositions useful in treating prostate cancer. The invention is based on BIRM, an extract of the plant *Solanaceae-Dulcamara* and its previously unrecognized anti-prostate cancer activity. Also disclosed are methods for preparing compositions for administration to humans for treating prostate cancer.

38 Claims, 7 Drawing Sheets

OTHER PUBLICATIONS

Smith, Michael, et al., "Select Complementary/Alternative Therapies for Prostate Cancer The Benefits and Risks", *Cancer Practice*, (2001),9:253-255.

Dandekar, Devendra S., et al., "An orally active Amazonian plant extract (BIRM) inhibits prostate cancer growth and metastasis", *Cancer Chemotherapy and Pharmacology*, (2003),52:59-66.

Harvey Wickes Felter, M.D. et al., "King's American Dispensatory" Homepage website, http://www.henriettesherbal.com/electic/kings/index.html, (Feb. 8, 2002).

John T. Cutis et al., "Wisconsin Botancia Information System (WIBIS)", http://www.botany.wisc.edu/wisflora/scripts/details.asp??SpCode=SOLDUL, pp. 1-2.

USDA Natural Resources Conversation Service (USDA-NRC), http://www.plants.usda.gov/java.profile?symbol=SODU, pp. 1-2/4.

Plant Atlas by USF; http://www.plantatlas.usf.edu/plantimage/solanum_dulcamara.jpg, color picture.

Plant Atlas by USF; http://www.plantatlas.usf.edu/plantimage/solanum_dulcamara.jpg, color picture.

Plant Atlas by USF; http://www.plantatlas.usf.edu/plantimage/solanum_dulcamara.jpg, color picture.

Gary A. Scott, Printout from garyascott.com website, http://www.garyascott.com, Make, enjoy and Keep Wealth, 1968-2006.

* cited by examiner

ANTI-PROSTATE CANCER COMPOSITION AND THERAPEUTIC USES THEREFOR

BACKGROUND OF THE INVENTION

Prostate cancer (CaP) is the most commonly diagnosed cancer in American men with an estimated 189,000 new cases in the year 2002 and the second most common cause of death from cancer in American men. (Jamel et al., Cancer J for Clinicians, 52: 23-47, 2002.) Prostate cancer, like other cancers, can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals, and, likewise, will cease dividing in the presence of inhibitory signals. In a cancerous or neoplastic state, a cell acquires the ability to "override" these signals and to proliferate under conditions in which a normal cell would not grow.

In general, tumor cells must acquire a number of distinct aberrant traits in order to proliferate in an abnormal manner. In addition to abnormal cell proliferation, cells must acquire several other traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue. In many cases cells ultimately acquire the capacity to metastasize to distant sites.

In the realm of cancer therapy it often happens that a therapeutic agent that is initially effective for a given patient becomes, overtime, ineffective or less effective for that patient. The very same therapeutic agent may continue to be effective over a long period of time for a different patient. Further, a therapeutic agent, which is effective, at least initially for some patients, is completely ineffective or even harmful for other patients.

Chemotherapy, androgen withdrawal, surgery and radiation therapy are some of the current forms of prostate cancer treatment. Androgen withdrawal, by castration or through the use of an anti-androgenic drug, is the preferred treatment method for prostate cancer. One drug used to initiate androgen withdrawal is Bicalutamide. Bicalutamide (casodex) is a relatively potent, orally active anti-androgenic drug. Approximately 80% of the prostate cancer patients treated with bicalutamide respond to the treatment; however, most patients eventually relapse. Indeed, no current treatment is completely effective. The majority of the CaP related deaths, estimated to be 30,200 in the year 2002, is likely a result of failure of all currently available conventional treatments.

Because of the problems associated with conventional therapy, or sometimes also the cost, CaP patients often seek unproven therapeutic approaches (Jacobson and Chetty (2001) Curr Oncol Rep 3:448-52.) In fact, poor efficacy of conventional chemotherapeutic drugs against metastatic hormone-refractory prostate cancer (CaP) drives patients to try "alternate medicine." It is estimate that 30%-40% of men with CaP experiment with one or more complementary therapies which include high dose vitamins and minerals, herbal preparations, plants and plant extracts, and supplements of soy, saw palmetto etc. (Jones et al., (2002) Urology 59:272-276.)

In view of the above considerations, it is clear that there is a need to supplement existing methods of inhibiting prostate cancer cell invasiveness and metastasis. Current approaches rely on highly cytotoxic compounds that cause ancillary debilitating sickness in patients, or use methodology that is expensive, procedurally difficult, and unpredictable. Accordingly, it would be useful to identify an anti-prostate cancer composition that is efficacious and well tolerated in humans.

SUMMARY OF THE INVENTION

"BIRM" is a natural herbal medicine, not previously associated with the treatment of CaP. BIRM stands for Biological Immune Response Modulator, and has been formulated by the applicant based on local folklore among the Ecuadorian native population. The formulation was dispensed as a natural remedy for a variety of maladies including HIV-1 infection and cancer (other than prostate cancer) (Cevallos EA (1994). Binational experience in the treatment of AIDS with a low molecular weight natural carbohydrate (ECA-10-142), as a stimulant of the immunology system $10^{th}$ Internatl. Conference on AIDS (Yokohama, Japan) Book of Abstracts Vol. 1 PA No. 0294; Cevallos EA (1996) "BIRM: La estrtegia terapeutica del futuro". Abstract of Congreso Mundial de SIDA en Vancouver; BIRM Carbohydrate of low molecular weight ECA10-142 controls AIDS (1994) $10^{th}$ Internatl. Conference on AIDS (Yokohama, Japan) Book of Abstracts Vol. 2 PA No. 0291.) Very little systematic information is currently available on BIRM and no studies have been undertaken to investigate structure-function correlation of ingredients in BIRM.

It has now been discovered that these and other long felt needs can be achieved by the present invention, which provides, in one aspect, methods for inhibiting the growth or development of prostate cancer in a mammal by providing BIRM, an extract of the plant *Solanaceae-Dulcamara* to a mammal in need of such treatment in an amount that is effective to achieve the specified result.

The invention features a method of treating a mammal with prostate cancer, or at risk of prostate cancer, comprising administering to the mammal a pharmaceutical composition comprising an effective amount of Biological Immune Response Modifier (BIRM). The method is useful for inhibiting growth of prostate cancer. The method comprises, inhibiting cellular proliferation of prostate cancer, inhibiting invasiveness of the prostate cancer, and/or inhibiting metastasis of prostate cancer. The BIRM formulation can be administered in an amount sufficient to specifically arrest prostate cancer cells in the $G_0/G_1$ cell-cycle phase, increase apoptosis and inhibit expression of hyaluronidase, an enzyme implicated in tumor angiogenesis and metastasis. The method can further comprise treating the mammal with an adjunct anti-prostate cancer modality. The adjunct anti-neoplastic modality can comprise chemotherapy, surgery, and/or radiotherapy. One aspect of the invention provides a method of inhibiting prostate cancer growth in a mammal, comprising administering to the mammal a cancer-inhibitory amount of BIRM.

By means of the invention, a method of killing prostate cancer cells or inhibiting prostate cancer cell growth or metastasis is provided that avoids or mitigates side effects commonly associated with anti-prostate cancer chemotherapeutic regimens, increases efficacy, or both. Another aspect of the invention involves a method of reducing side affects associated with treating CaP.

Another aspect of the present invention provides a method of preparing BIRM comprising: a) harvesting root samples from an Ecuadorian plant *Solanaceae-Dulcamara*; b) stabilizing the root samples; c) drying the root samples; d) modifying the root samples via oxidative reduction; and e)

isolating a plant extract from the root samples, wherein the plant extract comprises BIRM.

These and other aspects of the present invention will be better appreciated by reference to the following drawings and detailed description. The detailed description and examples enhance the understanding of the invention, but are not intended to limit the scope of the invention.

BRIEF DESCRIPTION OF THE DRAWINGS

Various embodiments of the invention have been chosen for purposes of illustration and description, but are not intended in any way to restrict the scope of the invention. The preferred embodiments of certain aspects of the invention are shown in the accompanying drawings, wherein:

FIG. 2. Effect of BIRM on the growth of CaP cells. A. Cells cultured at low density in 60-mm culture dishes were exposed to BIRM for 24 h. Surviving cells at the end of incubation were allowed to form adherent cell colonies during the next 7-10 days. Cell colonies stained with 0.1% crystal violet and colonies containing>50 cells were counted manually using a hand-held electronic counter in a blinded fashion. A: Colonies of surviving PC3-ML cells exposed to BIRM for 24 h. B: Clonogenic survival of CaP cells co-cultured with BIRM. Results are presented as Mean±SEM, obtained from 3 independent experiments.

FIG. 3. BIRM kills tumor cells by induction of apoptosis. PC-3ML, DU-145 and Mat Lylu cells CaP cells cultured in growth medium ($\times10^4$ cells/well; 48-well plates) with or without BIRM at various concentrations for 24 h were analyzed for apoptotic activity using the Cell Death ELISA Plus assay kit, which allowed us to measure the soluble nucleosomes by spectrophotometry. Data shown are Mean±SEM obtained from three independent experiments.

FIG. 4. BIRM induced increase in caspase activity. CaP cells were treated with BIRM for 4 to 24 h and total activities of cell-death associated caspases was measured using a kit that employs a rhodamine 110-conjugated peptide substrate common to all cell death-related caspases. Results presented are mean±SEM from three independent experiments. Caspase activity in untreated control cultures was detectable, but was typically 10x less than the activity detected in positive control provided with the assay kit.

DETAILED DESCRIPTION OF THE INVENTION

The present invention provides a method for treating prostate cancer. In accordance with the present invention, it has been found that compositions containing BIRM can be used to treat prostate cancer. "Treatment" and "treating" as used herein include preventing, inhibiting, curing, or alleviating growth of prostate cancer cells, prostate cancer or symptoms thereof, or preventing or alleviating the metastasis of prostate cancer.

Alleviating prostate cancer includes degrading a prostate tumor, for example, breaking down the structural integrity or connective tissue of a prostate tumor, such that the tumor size is reduced when compared to the tumor size before treatment. Inhibiting and/or curing prostate cancer includes degrading a prostate tumor such that the tumor cannot be detected by known diagnostic means for one year after treatment. Without being limited to any theory of operability, the tumor may be reduced in size or become undetectable, for example, by atrophying from lack of blood supply or by being attacked or degraded by one or more components administered according to a method of the invention.

Alleviating metastasis of prostate cancer includes reducing the rate at which the prostate cancer spreads to other organs. Preventing metastasis of prostate cancer includes preventing the prostate cancer from spreading outside of the prostate.

A treatment according to the invention may be carried out by administering a composition including BIRM in an amount effective for alleviating, curing, inhibiting, or preventing prostate cancer or preventing or alleviating the metastasis of prostate cancer. BIRM is an aqueous oral formulation currently available from BIRM, Inc. (Quito, Ecuador). BIRM contains a number of yet to be identified compounds. If one or more of these compounds is found to be therapeutically effective alone, or in some subgroup of other BIRM constituents, the administration of that agent, alone, or as part of a formulation, at concentrations at least as that found in a 5 ml sample of commercial BIRM is contemplated. The recommended minimum dosage of BIRM useful in treating CaP is 5 ml/12 hours and the recommended maximum dosage of BIRM useful in treating CaP is 5 ml/6 hours.

The formulation useful according to the invention possesses a desirable but unusual combination of physicochemical properties, including activity, bioavailability, solubility, and reduction of side effects. These properties render the formulation particularly desirable for the treatment of prostate cancer.

BIRM exhibits its prostate cancer-inhibitory properties at concentrations that lead to fewer side effects than those of known chemotherapeutic agents, and in some cases are substantially free of side effects. In addition, it is believed that the properties of hydrophilicity and hydrophobicity are well balanced in BIRM, enhancing its utility in vivo, while other compounds lacking such balance are of substantially less utility. Specifically, BIRM has an appropriate degree of solubility in aqueous media to permit absorption and bioavailability in the body, while also having a degree of solubility in lipids to permit traversal of the cell membrane to a putative site of action.

The invention includes a method of inducing cytotoxicity (cell killing) in prostate cancer cells or reducing the viability of prostate cancer cells. The cytotoxicity of BIRM can be exploited preferably against prostate cancer. The mechanism by which this cytotoxicity occurs is not completely understood, but the selective killing of the cancer cells can occur through apoptosis, necrosis, another mechanism, or a combination of mechanisms.

BIRM appears to exhibit its beneficial effect in a dose-dependent manner. Thus, within broad limits, administration of larger quantities of BIRM has been observed to inhibit prostate cancer cell growth or invasiveness to a greater degree than does administration of a smaller amount. Moreover, efficacy has been observed at dosages below the level at which toxicity is seen in normal cells or in subjects. Accordingly, one of the advantages of the invention is that the debilitating side effects usually attendant upon conventional cytotoxic prostate cancer treatments are reduced, and preferably avoided.

Dosage Forms: Specific examples of pharmaceutical acceptable carriers and excipients that may be used to formulate oral dosage forms of the present invention are described in U.S. Pat. No. 3,903,297 to Robert, issued Sep. 2, 1975.

Techniques and compositions for making dosage forms useful in the present invention are described herein below.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary or paste.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin and cyclodextrin derivatives and the like.

Capsule or tablets can be easily formulated and can be made easy to swallow or chew. Tablets may contain suitable binders, lubricants, diluents, disintegrating agents, coloring agents, flavoring agents, flow-inducing agents, and melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethlcellose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or betalactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Molded tables may be made by molding in a suitable machine a mixture of the powdered active ingredient moistened with an inert liquid diluent.

The tablets may optionally be coated or scored and may be formulated so as to provide slow or controlled release of the active ingredient. Tablets may also optionally be provided with an enteric coating to provide release in parts of the gut other than the stomach.

Formulations suitable for buccal administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Formulations suitable for oral administration may be administered in the form of an emulsion. The oil phase of the emulsions of the composition used to treat subjects in the present invention may be constituted from known ingredients in a known manner. This phase may comprise one or more emulsifiers. For example, the oily phase comprises at least one emulsifier with a fat or an oil or with both a fat and an oil or a hydrophilic emulsifier is included together with a lipophilic emulsifier, which acts as a stabilizer. Together, the emulsifier(s) with or without stabilizer(s) make up an emulsifying wax, and the wax together with the oil and/or fat make up the emulsifying ointment base which forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, parrafm, straight or branched chain, mono- or dibasic alkyl esters, mineral oil. The choice of suitable oils or fats for the formulation is based on achieving the desired cosmetic properties, the properties required and compatibility with the active ingredient.

The maximal dosage for a subject is the highest dosage that does not cause undesirable or intolerable side effects. For example, BIRM can be administered in an amount of from about 0.1 µl/kg/day to about 100 µl/kg/day, and preferably from about 1 µl/kg/day to about 20 µl/kg/day. These dosage ranges represent quantities of the various components of the composition that are therapeutically effective for treating prostate cancer. But the dose of the composition can vary depending on the age of the patient, nature and severity of disease, and potency of the composition. For the purpose of the present invention, side effects may include clinically significant adverse activity, as well as toxic effects. In any event, the practitioner is guided by skill and knowledge in the field, and the present invention includes, without limitation, dosages that are effective to achieve the described phenomena.

The preferred pharmaceutical composition for use in the method of the invention includes a combination of BIRM in a suitable pharmaceutical carrier (vehicle) or excipient as understood by practitioners in the art.

The present invention additionally includes administering BIRM for use in the form of veterinary formulations, which may be prepared, for example, by methods that are conventional in the art.

Useful pharmaceutical dosage forms for administration of the compounds of this invention are illustrated as follows:

Enteral administration is a preferred route of delivery of BIRM, and compositions including BIRM with appropriate diluents, carriers, and the like are readily formulated. Liquid or solid (e.g., capsules, soft gelatin capsules, tablets, solutions, and suspension) formulations can be employed. It is among the advantages of the invention that, in many situations, BIRM can be delivered orally, as opposed to parenteral delivery (e.g., injection, infusion), which is typically required with conventional chemotherapeutic agents.

A large number of unit capsules may be prepared by filling standard two-piece hard gelatin capsules each with 100 μl-1000 μl of active ingredient, 150 milligrams of lactose, 50 milligrams of cellulose, and 6 milligrams magnesium stearate.

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

A large number of tablets are prepared by conventional procedures so that the dosage unit was 100 μl-1000 μl of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

An aqueous solution or suspension is prepared for oral administration so that each 5 ml contain 100 μl-1000 μl of active ingredient, 200 mg of sodium carboxymethyl cellulose, 5 mg of sodium benzoate, 1.0 g of sorbitol solution, U.S.P., and 0.025 ml of vanillin.

A parenteral composition suitable for administration by injection is prepared by stirring 1.5% by weight of active ingredient in 10% by volume propylene glycol and water. The solution is made isotonic with sodium chloride and sterilized.

Techniques and compositions for making dosage forms useful in the present invention are described in the following references: 7 Modern Pharmaceutics, Chapters 9 and 10 (Banker & Rhodes, Editors, 1979); Lieberman et al., Pharmaceutical Dosage Forms: Tablets (1981); and Ansel, Introduction to Pharmaceutical Dosage Forms 2nd Edition (1976).

BIRM can be co-administered e.g., combined, with other chemotherapeutic agents or potentiators.

*Solanaceae Dulcamara* contains at least two naturally occurring therapeutic ingredients, low molecular weight monosaccharides (between about 3,500 and about 10,000; and ≧ about 30,000) and medium molecular weight nucleotides (between about 50 nucleotides and about 500 nucleotides), which are biotechnologically modified by reductive cell cultures to produce BIRM. The process of converting *Dulcamara* plant raw materials to BIRM generally entails (i) collecting botanical samples, (ii) stabilizing the harvested samples, (iii) drying the samples, and (iv) isolating the desired plant extract through reductive fermentation.

Botanical raw materials used to make BIRM may be harvested when the active ingredient is present in the largest amount (e.g., roots, rhizomes, bulbs, and tubercules in the spring or fall; flowers at the time of blooming; leaves and buds immediately prior to full growth) and in an excess of 10% above the theoretical content of the raw materials desired because degradation begins immediately after harvest. Harvesting a true representative sample of botanical raw materials provides uniformity in subsequent batches of plant extract.

Harvested plants may be cleaned to remove foreign material or unusable portions and stored so as to prevent infestation by insects or rodents, accumulation of dirt, and decomposition through the action of microorganisms, enzymes, catalysts, yeast, bacteria, and mold.

Harvested botanical samples may be stabilized by enzyme destruction or inhibition. Stabilization by enzyme destruction is more common and generally requires temperatures between 79° C. and 110° C. and may involve gaseous agents, vapors of organic substances such as alcohol or water vapor, or liquid alcohol, which reduces the production of extracts or alcoholates. Stabilization may also involve the use of enzyme inhibitors. Enzyme inhibition is defined herein as reversible inhibition of enzymatic activity associated with the harvested botanical samples. Such inhibition may be achieved using many drugs and toxic agents, such as for example, protease inhibitors or chelating agents.

One method of stabilization involves exposing harvested samples to UV rays and ultrasound. Although this method has yielded good results, it is not used frequently.

A second method employs drying harvested samples at temperatures between 20° C. and 120° C. in ventilation-type ovens, between 20° C. and 150° C. in ovens in which the pressure can be varied, and between 20° C. and 180° C. in infrared ovens. In all three oven types, the material initially dries rapidly and stabilizes and heating continues until the sample becomes brittle. (Nguyen-Hiep, (1965) Ann Pharm Fr. 23(5):297-305.)

A third method involves using autoclaving and alcohol vapors to stabilize a sample. In one variation of this method, a small amount of alcohol is placed in a common autoclave instead of water. Depending on the nature of the material, the autoclaving process continues for one to five minutes at 0.5 ATM and then is allowed to cool and depressurize. After removal, the sample fragments may be placed in an oven to eliminate the residual alcohol. In a second variation, alcohol vapors are produced in a boiler with a coil and passed to the chamber of an autoclave where the harvested samples are located. When enzyme destruction is complete, communication between the boiler and the autoclave is disconnected and the sample's alcohol content is measured by heating from the steam in double wall of the autoclave and collected the resulting vapor with a condenser.

Methods of enzyme destruction may be used simultaneously with methods of enzyme inhibition.

In general, dry samples remain stable for 24 months without sterilization and 48 months when sterilized.

Sample drying involves a process that is uniform, natural, and allows control over the temperature, moisture content of the root, and regulation of external humidity to prevent decomposition by fungi or yeast and putrefaction. Samples may be dried by solar drying when sun exposure is controlled.

Solar drying regulates the intensity and duration of sun exposure while enhancing desirable effects including the amounts of thermal energy, light, and radiation beneficial to the biotransformation of certain organic substances received from the sun, and limiting undesirable effects including elevated temperature and glare due to direct illumination of excessive intensity.

Solar driers may be constructed from a variety of materials. Solar driers made from wood and glass are beneficial when insect infestation is a threat to sample viability. Solar driers made from wood and transparent plastic sheet may be used when the plastic is nontoxic and does not emit volatile substances. Solar driers may also be boxes made of wood with wooden trays or access for rapid drying Oxidative reduction generally involves an oxidation step during which compounds lose electrons (e.g., to an oxidizing agent such as NAD+) followed by a reduction step during which those compounds gain electrons (e.g., from a reducing agent such as NADH). By way of example only, oxidative reduction of *Dulcamara* may be accomplished by fermentation.

Reductive fermentation involves adding dry botanical sample material at a concentration equivalent to 10% of the sample material's dry weight, and equivalent to 90% distilled water in a two-step fermenter. The first step of fermentation proceeds for 10 hours at 110° C. under controlled oxygen.

Specific enzymatic organic materials may be added during the second step of the fermentation process.

When samples of the mixture are removed from the fermenter the botanical extracts may be isolated by evaporating the mixture's solvents and adjusting the residual mass or powder according to prescribed standards. Alternatively, botanical extracts may also be isolated by extraction by percolation. In this latter method, the total filtrates are generally concentrated by distillation under reduced pressure to avoid too much heat exposure.

Products' composition may be identified using Fehling's reaction, thin layer chromatography (TLC), nuclear magnetic resonance (NMR), spectroscopy, or a combination thereof. Analytical TLC may be modified to obtain a higher rate of reaction by alternating the concentration of the elements while using the same substrate base.

Nucleotides may be mixed in the fermenter after BIRM's oligomonosaccharide content is evaluated. The extract consists of oligomonosacharides and nucleotides of a high pure grade.

The following examples are provided to assist in a further understanding of the invention. The particular materials and conditions employed are intended to be further illustrative of the invention and are not limiting upon the reasonable scope thereof.

Figure 1:
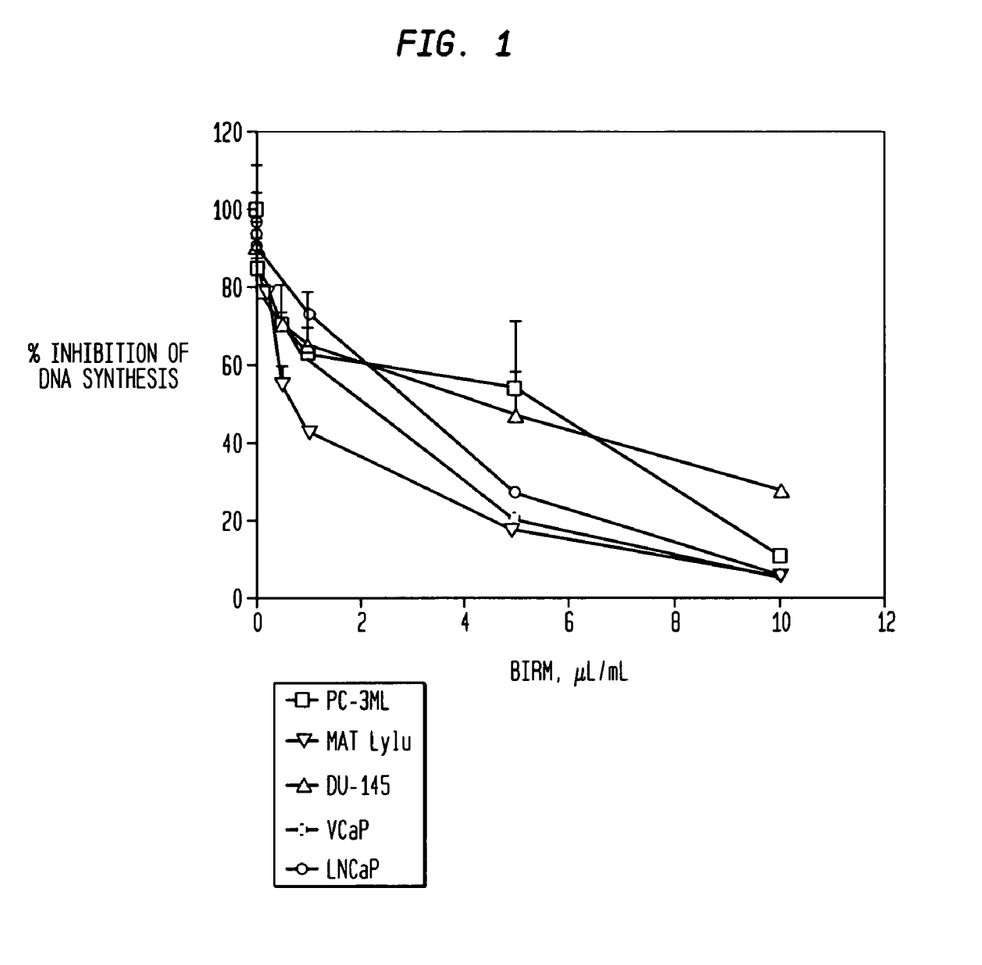
FIG. 1. Cytotoxicity of BIRM on prostate tumor cell lines: CaP cells cultured in growth medium ($1\times10^4$ cells/well; 48-well plates) were exposed to various concentrations of BIRM. Following incubation for 24 h, DNA synthesis was determined by measuring $^3$H-thymidine incorporation in the proliferating cells. Vertical bar represents Mean±SEM, from three independent assays.
Figure 2A:
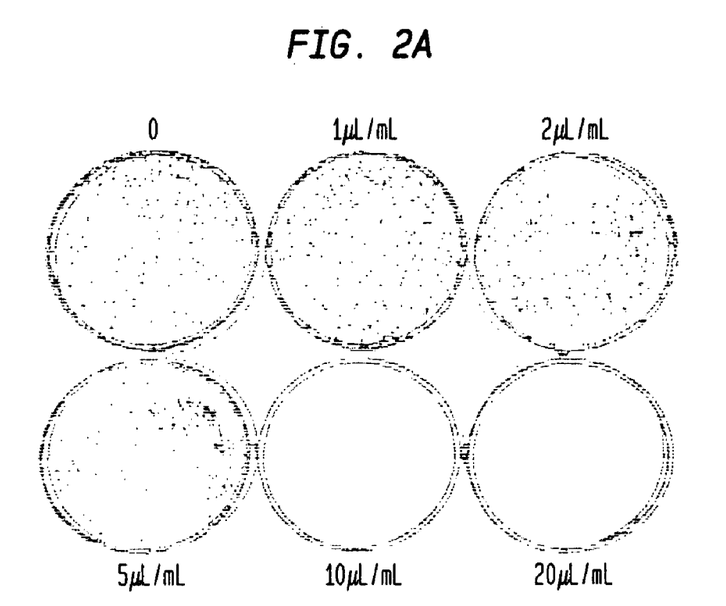
Figure 2B:
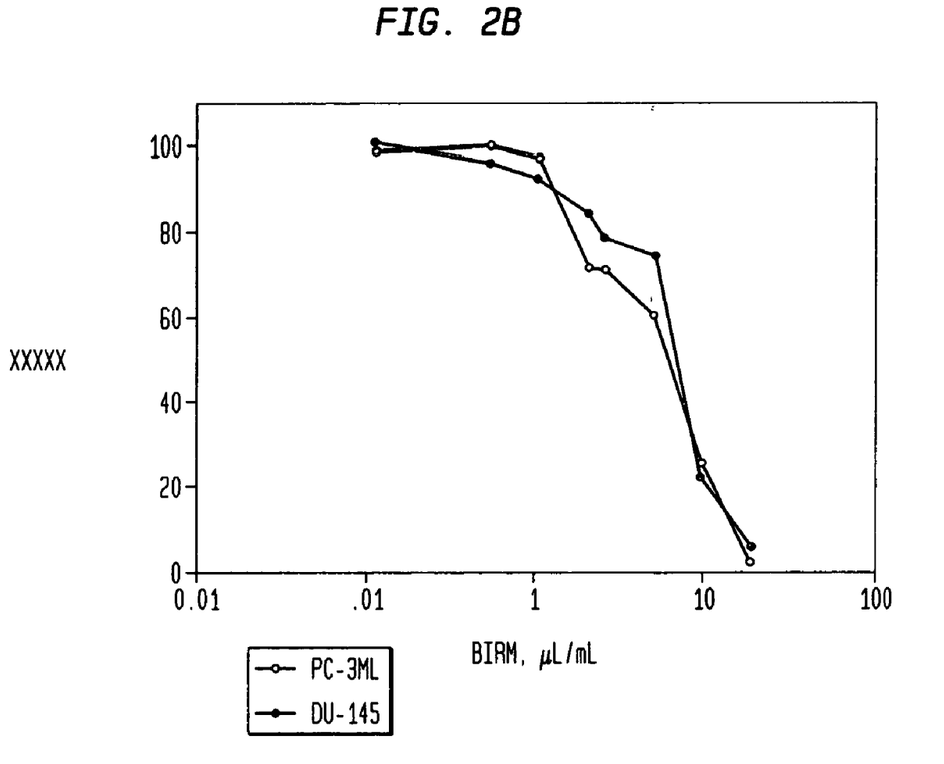
Figure 3:
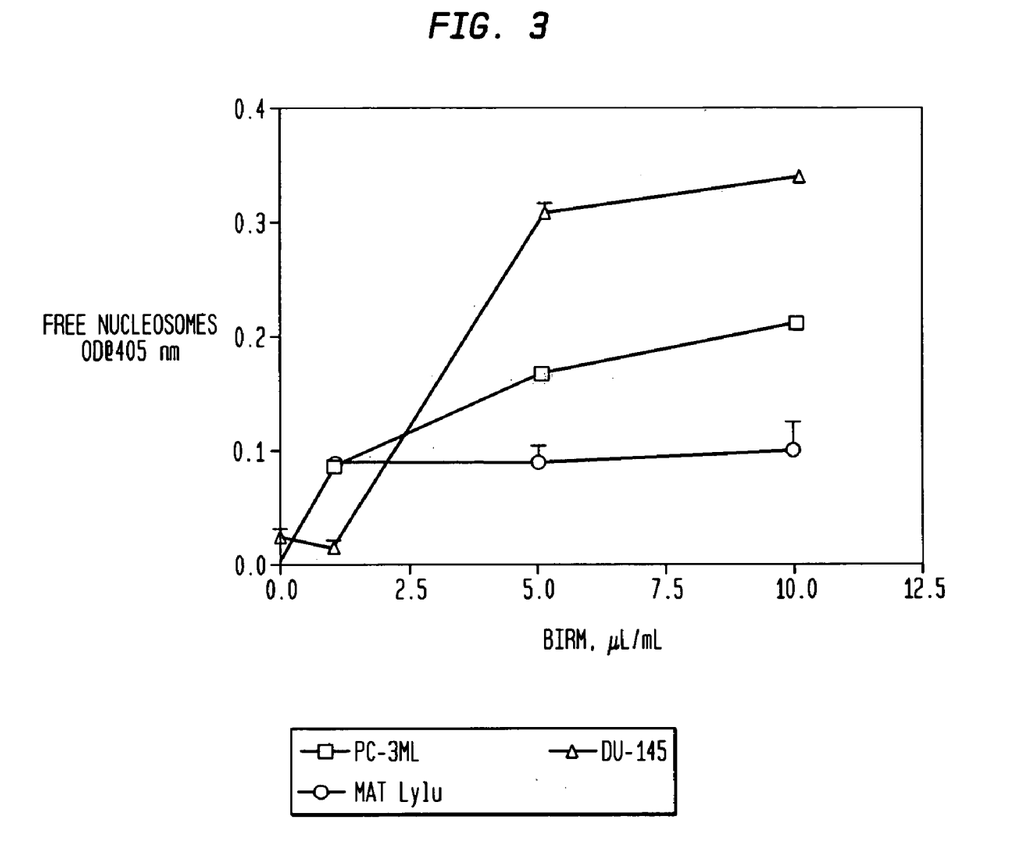
Figure 4:
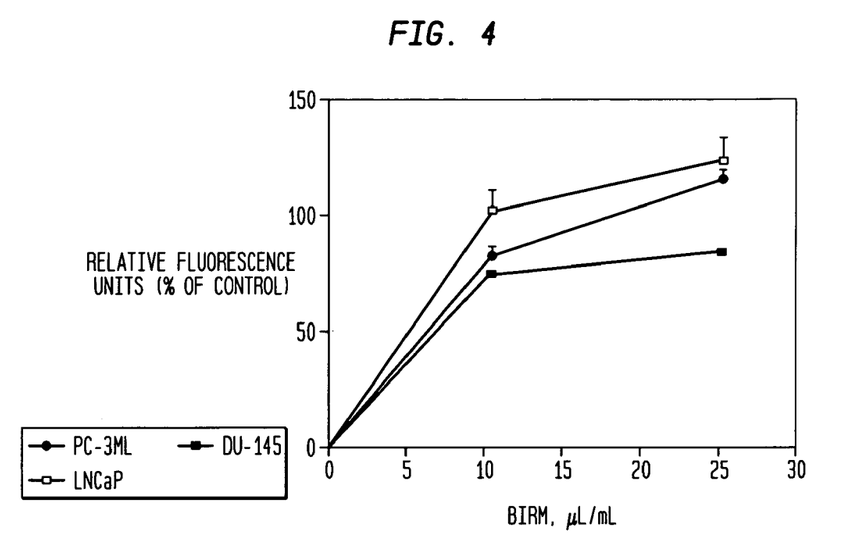
Figure 5:
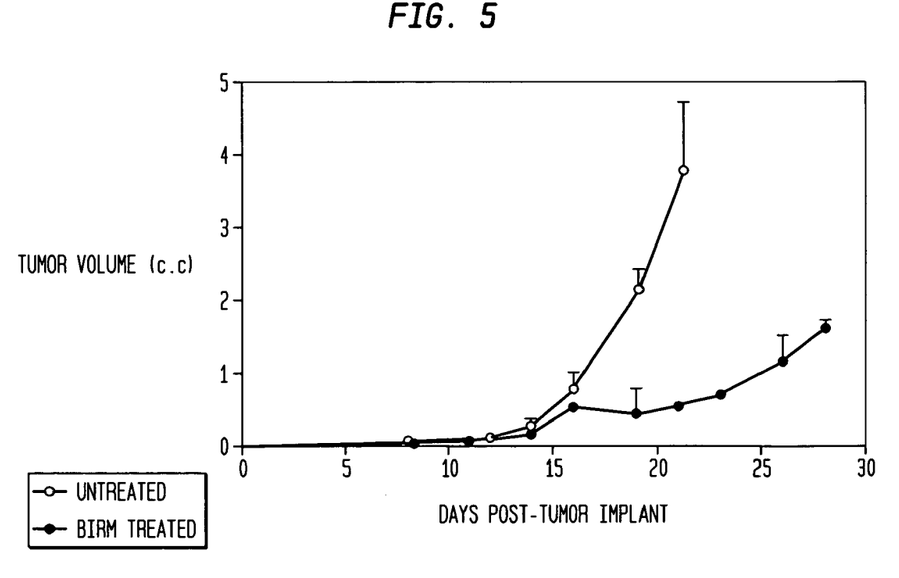
FIG. 5. Effect of daily dosing of BIRM on growth and metastasis of Dunning MAT LyLu tumors in rats. Tumor growth in rats with subcutaneous tumor implants with EGFP-MAT Lylu cells ($2\times10^5$ cells/animal). Data presented are mean±SEM of each treatment group over time. Data from control group includes measurements of 6 tumor bearing rats, whereas the BIRM treated group had only 4 animals in the group, other 2 animals in this group did not develop tumors.
Figure 6:
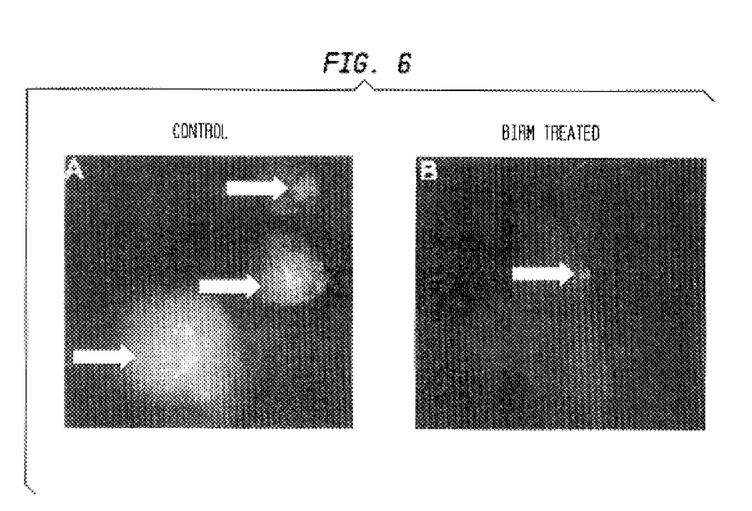
FIG. 6. EGFP-MAT LyLu rat prostate tumors metastatic to lungs. The figure shows rat lungs with fluorescent tumor foci (indicated with arrows). A: Control animals (magnification 40x). B: a typical tumor metastatic to lung in BIRM treated group (magnification 20x). Tumors foci in BIRM treated animals were typically 10x smaller or absent in lungs.

The invention is based, in part, on the identification of the anti-proliferative effect of BIRM on prostate cancer. The medicinal value of BIRM is believed to be associated only with the Amazonian variety of *Dulcamara*, where the micronutrients present in the soil of upper Amazon basin promote the synthesis of the medicinal compounds in the plant. BIRM inhibits cell proliferation and clonogenic survival (FIGS. 1 and 2) and undergo apoptotic cell death via caspase activation pathway (FIGS. 3 and 4). In-vivo studies on the growth and metastasis of Dunning MAT LyLu tumors suggest that oral dosing with BIRM results in low tumor incidence, slow tumor growth and reduced spontaneous metastasis to lungs (FIGS. 5 and 6A, B). A preliminary biochemical characterization and size exclusion chromatography data suggest that there are at least 4 active species present in BIRM, 3 have cytotoxic activity and the $4^{th}$ has HAase inhibition activity. All 4 active ingredients in BIRM are heat stable and unlikely to be proteins or lipid-soluble compounds.

EXAMPLE 1

Test Compound. BIRM is an aqueous extract of dried roots of a plant (genus *Dulcamara*, family *Solanaceae*), grown in Ecuador, marketed as a greenish-brown suspension having a mild bittersweet smell. The inactive ingredients in BIRM contained 16% solids, root fibers, and the remainder, lipid-free liquid. In general, BIRM is prepared by aqueous extraction of dried roots followed by oxidation-reduction of the extract. More specifically, BIRM is prepared by a process comprising (a) isolating roots from the Ecudorian plant *Solanaceae-Dulcamara*; (b) cooking up to the boiling point of the *Solanaceae-Dulcamara* roots; (c) diluting 4 ounces of the *Solanaceae-Dulcamara* roots with 1000 ccm of distilled water; (d) incubating the resultant mixture at room temperature for 10 hours; and (e) reductive oxidation, by fermentation, to obtain the anti-prostate cancer composition. During this process, the amount of roots and the timing of oxidation/reduction are carefully controlled to minimize batch-to-batch variation.

In one aspect of the invention, the process of reductive fermentation of BIRM comprises: (a) milling 936 kg dry *Solanaceae-Dulcamara* roots in a mill of stainless steel until granulated about 5 mm in diameter ; (b) drying the milled material at 55° C. in a solar oven until the material was about 88% dry; (c) mixing the resultant dry material with culture media equivalent to 33% of the *Dulcamara's* dry weight; (d) adding the milled dry material of step (c) to a 2 step stainless steel fermentator; (e)adding an additional amount of 33% dry *Dulcamara* roots to the fermentor; (f) incubating the material in the fermentor for 14 hours at 74-77° C. under controlled oxygen (1 liter per minute of oxygen); and (g) adding 500 gm of catalase to the fermentative.

In a further aspect of the invention, the process of making BIRM comprises: (a) adding 4485 kg of distilled water to the fermentation reactor at 50° C.; (b) slowly adding over a few minutes 936 kg of dry dulcamara material from step (g) of the reductive fermentation process; (c) mixing the resultant mixture of step (b) for several minutes; (d) closing the reactor; (e) elevating the temperature of the reactor to 100° C.; (f) mixing the reaction materials continuously for 15 minutes; (g) shutting the heat off the reactor; resting the reactor containing the material for 10 hours, (h) transfering the material to the 2 step fermented process. (see step c and d above); (i) filtering the mixture under 50 kg/cm$^2$ pressure, using a filter press of canvases or similar material, with an aproximate pore size of 2 mm, to obtain a natural filtrate; (I) adding 0.45 kg sodium metabisulfite to the filtrate to obtain BIRM. The resultant BIRM material was added to 5 tightly closed gallon containers and sealed, indicating the final preparation.

The efficacy of BIRM samples from five different batches prepared in this manner were selected randomly and tested on two different cell lines (PC-3ML and LNCaP) by MTT assay to determine inter-batch variation, if any. No inter-batch variation in the potency of BIRM for induction of cytotoxicity was observed. For all examples described herein, a clarified BIRM, obtained by centrifugation at 10,000-xg was used.

EXAMPLE 2

Production and Properties of BIRM. *Dulcamara* is harvested when the plant has grown for 14 months and the roots have a length of between about 15 to about 25 cm.

Three batches of dry *Solanacea-Dulcamara* plants were received from the Ecuadorian Tumor Institute: 3.8 kg (30% moisture), 3.6 kg (31.4% moisture), and 5.3 kg (32.2% moisture). After grinding, the *Dulcamara* plants were dried in a solar drier at 55° C. for 4 hours to avoid direct sunlight.

The solar dryer used regulated insolation passively and utilize free energy emitted by the sun through adequate uptake, storage, and consumption. This helped regulate temperature and humidity and allowed grains, vegetables, and medicinal plants to be dried.

The mixture used in reductive fermentation was made in proportional parts according to indications and in an amount equivalent to 88% of the dry *Dulcamara*. Dry *Dulcamara* and culture media equivalent to 33% of the *Dulcamara's* dry weight was placed in the two-step fermenters and developed for 14 hours at 74-77° C. with controlled oxygen. The specific enzymatic organic material was added to the second step of the fermentation reactor.

Samples of the culture medium were extracted from the fermenter for isolation of the plant extract BIRM.

Fehling's reaction was used to determine BIRM's composition in all three batches. The analysis revealed that BIRM contained low-molecular-weight oligomonosaccharides (1% Fehling liquor). BIRM contained 15.92% total sugars, including of glucose, fructose, 1-ketose, and 1-beta-furanosyl fructose fractions. TLC also identified traces of bio-organic minerals, primarily calcium and magnesium. NMR analysis of BIRM's molecular structure confirmed the presence of double oligomonosaccharides of calcium and magnesium in its racemic form of hydroxyethyl malonate, giving the oligomonosaccharides present in BIRM a condensed molecular formula of $(C_7H_9O_6 \cdot Mg \ldots Ca)_n$ and a molecular weight of $(251.38)_n$ (where n=1 or a multiple of 1). BIRM's extended molecular formula is:

Ecuador Pat. No. PI 02-1718 (published Mar. 8, 2002).

Composition analysis by spectroscopy revealed the following results (Table 1):

TABLE 1

Chemical Composition of BIRM

| Chemical Composition | Concentration (ppm or mg/L) | Limits |
|---|---|---|
| Aluminum (Al) | 10 ppm | No more than 50 mg/liter |
| Calcium (Ca) | 300 ppm | No less than 500 mg/liter |
| Iron (Fe) | 10 ppm | No more than 50 mg/liter |
| Magnesium (Mg) | 50 ppm | No less than 30 mg/liter |
| Manganese (Mn) | 50 ppm | No less than 30 mg/liter |
| Silicon (Si) | 1000 ppm | No less than 500 mg/liter |
| Zinc (Zn) | 10 ppm | No less than 5 mg/liter |

BIRM also contained therapeutic medium molecular weight nucleotides. The nucleotides are isolated from the mixture by conventional methods. Birm treatment always includes both the sugar content and the nucleotide content.

In filtered solution, BIRM had a dark reddish-brown color, tasted slightly sweet, smelled slightly sugary, appeared to be a molecular mass of oligomonosaccharides in a viscous solution, was stable in a concentration of 12,000 cells/ml, and could be agitated moderately without altering its texture. It was stable stored in glass or nontoxic PVC containers, hermetically sealed at ambient temperature (10-35° C.), and protected from light.

When filtered through a mesh of 0.42 microns of a Millipore filter, BIRM resembled a soft paste of white rhombic crystals. When dried in a vacuum oven at 55° C., a uniform amorphous product of soft texture and slightly sweet taste was obtained. This form of BIRM may be stored in a dry place in hermetically closed containers protected from direct sunlight. Other physical and chemical properties of BIRM are listed in Table 2.

TABLE 2

Physical-Chemical Properties of BIRM

| | |
|---|---|
| Density | 1.088 in a concentration of 22.5 × 10/mL |
| PH | 7.1 (1 g/710 ml of distilled water) |
| Solubility | soluble in cold water very soluble in hot water soluble in alcohol |
| Percentage Sugars | no less than 14% reductive sugars with Fehling liquor at 1% |

EXAMPLE 3

Sugar Content of BIRM Samples. Composition analysis was performed on a solid sample of 2.8 kg (30.1% moisture) of oligomonosaccharides BIRM (Lot CP-I) and a liquid sample of 5.2 liters of oligomonosaccharides BIRM (Lot VP-II) from the Tumor Institute. Lots CP-I and VP-11 contained 17.1% and 16.8% total sugars, respectively.

EXAMPLE 4

Cells and tumor lines. Established human CaP cell lines: LNCaP and DU-145 cells were obtained from ATCC, Rockville, Md. A recently established bone metastic, PSA+ CaP line (i.e., VcaP) was obtained by Drs. Pienta and Cooper (Karmanos Cancer Center, University of Michigan, Ann Arbor Mich.) (Mickeyet et al., (1980) Prog Clin Biol Res 37:67-84; Horoszewicz et al., (1983) Cancer Res 43:1809-1818; Korenchuk et al., (2001) In Vivo 15:163-168.) A metastatic variant of PC-3 cells, PC-3ML was obtained from Dr. Mark E. Stearns, Allegheny University Hospitals, Philadelphia, Pa. (Kaighn et al., (1979) Invest Urol 17:16-23; Wang and Stearns (1991) Differentiation 48:115-125.) All the cultures were maintained in a complete medium (CM) containing RPMI 1640 basal medium, 10% fetal bovine serum (Atlanta Biologicals, Atlanta, Ga.), and 10 μg/ml gentamicin. The EGFP-MAT LyLu cell line was generated by stable transfections of Dunning MAT LyLu at rat CaP cells with pEGFP-1 plasmid DNA (Clontech, Calif.) and maintained in CM with 250 nM dexamethasone as described before. (Wenger et al., (1984) Urol 131:1232-1236; Lokeshwar et al., (2002) Internatl J. Cancer 98:297-309.)

EXAMPLE 5

Growth inhibition assay. $^3$H-thymidine incorporation assay was performed as described previously. (Dudak et al., (1996) Anticancer Res 16:3665-3671.) Following incubation in medium containing BIRM or without BIRM, the cells were pulse labeled with $^3$H-thymidine (1 μCi/ml) for 2 h. Incorporation of $^3$H-thymidine into cellular DNA was stopped with 10% trichloroacetic acid and the acid precipitable radioactivity was determined by liquid scintillation counting. (Dudak et al., (1996) Anticancer Res 16:3665-

3671.) Clonogenic survival of CaP cells exposed to BIRM for 24 h was assayed by the colony assay as described before. (Dudak et al., (1996) Anticancer Res 16:3665-3671.)

EXAMPLE 6

Determination of apoptosis activity. BIRM-induced apoptosis was assayed using a cell death ELISA kit (Cell death ELISA-Plus kit, Roche Molecular Biologicals). The assay measured the amount of free nucleosomes in cell lysate resulting from programmed cell death. (Boehringer Mannheim handbook on apoptosis and cell proliferation (1998) $2^{nd}$ ed. 138pp. Boehringer Mannheim, Germany.) Following treatment of BIRM for 4 h or 24 h on CaP cells, the amount of free nucleosomes present in lysate of cells undergoing apoptosis was estimated as per the supplier's instructions.

EXAMPLE 7

Cell-Cycle Analysis. CaP cells ($1\times10^5$) were cultured in 60-mm culture dishes. After an overnight culture, the cells were treated with 10 μg/ml of BIRM for 24 h. BIRM treated and untreated cells were harvested and stained with 50 μg/ml propidium iodide. The amount of propidium iodide bound to DNA was profiled in an EPICS XL flow cytometer as described previously. (Lokeshwar et al., (2002) Internatl J. Cancer 98:297-309.) The fraction of dead cells at the time of harvesting was about 16% as determined by trypan blue exclusion. The majority of these cells were floating, so were discarded at the time of washing. The remaining dead cells were gated out using the forward angle light scatter and side scatter gatings during flow cytometry. About 20,000 propidium iodide-stained cells were analysed in the flow cytometer from each sample. The MODFIT LT program (Verity Software House, Topsham, Me.) was used for the cell-cycle-phase analysis. (Yamamura et al., (1995) Cell Mol Biol 41:121-132.)

EXAMPLE 8

Determination of activation of cell death-caspases. Caspase activation in CaP cells treated with BIRM was determined using a kit (Homogenous Caspases Assay, fluorimetric kit, Roche Molecular Biologicals), which helped determine collectively activated caspases # 2, 3, 6, 7, 8, 9 and 10. The assay measures the free Rhodamine 100 (R110), resulting from the cleavage of a common caspase substrate conjugated to R110. Free R110 was determine fluorimetrically at 528 nm (maxima $\lambda_{ex}$=499 nm and $\lambda_{em}$=528 nm) and it is expressed as relative fluorescence units (RFU). (Homogeneous caspase assay (2002) Fluoriemtric. Roche Applied Science product handbook.)

EXAMPLE 9

Hyaluronidase (HAase) assay. In one aspect of the invention, the affects of BIRM on HAase activity secreted in DU-145 cell conditioned medium and partially purified HYAL1 using a HAase activity ELISA-like assay was examined. (Lokeshwar et al., (1996) Cancer Res 56:651-657; Block et al., (2001) J Biol Chem 276:11922-11932.) HYAL1 type HAase was partially purified from the urine of high-grade bladder cancer patients as described previously. (Lokeshwar et al., (1996) Cancer Res 56:651-657.) The assay was performed in a 96-well microtiter plate coated with HA (200 μg/ml, ICN Biomedicals). Wells were incubated with various concentrations of BIRM or column fractions from a Sephadex G-50 gel-filtration column (see below) in a HAase assay buffer at 37° C. for 15-hr. (Lokeshwar et al., (1996) Cancer Res 56:651-657.) Following incubation, degraded HA by HAase was washed off and the HA remaining in the microtiter wells was estimated, using a biotinylated bovine nasal cartilage-HA binding protein, and an avidin-biotin detection system (Vector Labs, Burlingame, Calif.). (Lokeshwar et al., (1999) Cancer Res 59:4464-4470.)

EXAMPLE 10

Biochemical characterization of cytotoxic activity in BIRM. To study heat activation, BIRM was heated at 100° C. for 5 min in a water bath. BIRM was digested with Proteinase K (10 U/ml) at 37° C. for 18 h. For size fractionation studies, clarified BIRM was loaded on Millipore ultra filtration mini Centriprep tubes (Millipore Inc. Bedford, Mass.) with membrane barriers with different molecular weight cut-off (i.e., MR~3.5 kDa, MR~10 kDa and MR~30 kDa). Following three cycles of centrifugation and separation of the low molecular weight fractions, both the filtrate and the retentate were assayed for cytotoxic activity. BIRM solution was also treated with charcoal-dextran (50 mg/ml) at 4° C. for 12 h to remove lipids and steroids (if any) present in BIRM. Following various treatments, BIRM was centrifuged and various concentrations of the supernatant were added to PC3-ML cells cultured in 24-well plates ($2\times10^4$ cells/well). BIRM-induced cytotoxicity was estimated using the MTT reduction assay following a 24 h-treatment. (Lokeshwar et al., (2002) Internatl J. Cancer 98:297-309.)

EXAMPLE 11

Gel filtration chromatography. Particle-free BIRM was loaded on a G-50 Sephadex column (1.5×120 cm) equilibrated with 20 mM Tris.HCI, pH 7.4 containing 150 mM NaCl buffer (Tris/NaCl buffer). (Lokeshwar et al., (1996) Association of elevated levels of hyaluronidase, a matrix-degrading enzyme, with prostate cancer progression. Cancer Res 56:651-657.) The column was eluted in Tris/NaCl buffer at 7 mL/hr and 3 mL fractions were collected. Each fraction was assayed for protein (BCA-BioRad), uronate (Bitter and Muir (1966) J. Clin Invest 45:963-975), inhibition of cell growth (MTT assay) (Lokeshwar et al., (2002) Internatl J. Cancer 98:297-309) and inhibition of HAase activity (Haase ELISA-like assay).

EXAMPLE 12

Inhibition of tumor growth by BIRM. Inhibition of growth of tumor by BIRM in the Dunning rat by oral administration of BIRM clearly suggests that the active ingredient(s) of BIRM are absorbed in the gastro-intestinal tract. Reduction in tumor incidence also suggests possible presence of anti-angiogenic agent(s). In the BIRM solution, which may also be responsible for the significant difference in size and number of tumor foci in lungs of animals treated with BIRM. It is estimated that 20-40% of patients initially diagnosed with local CaP have either locally advanced disease (stage C) or metastatic disease (stage D) (Harris and Reese (2001) Drug 61:2177-2192; (1995); Kojima et al., Urology 45:807-812) and the cure of the metastatic disease still remains a challenge. In the instant invention CaP cell cultures treated with BIRM show a significant reduction in cell proliferation and undergo apoptosis (FIGS. 1-3). This data indicates that active ingredients present in BIRM can be potentially used for controlling advanced hormone refractory prostate cancer. In the instant invention it was evaluated whether the BIRM-induced cytotoxic effect is due to inhibition of mitotic spindle separation. This would lead to a mitotic inhibition and arrest of cells in the G2/M-phase. Unexpectedly the data revealed that incubation with BIRM arrested CaP cells in $G_0/G_1$, which was compensated by a significant decreased (i.e., −56%) in the fraction of cell population in S-phase and a modest decrease in G2/M, thereby indicating a lack of mitotic arrest or cytokinesis (Table 3).

TABLE 3

Cell-cycle phase fractions (%) of PC-3 ML cells treated with BIRM for 24 h [a].

| Treatment | $G_0$-$G_1$ phase | Difference [b] | S phase | Difference | $G_2$-M phase | Difference |
|---|---|---|---|---|---|---|
| Control | 56.37 ± 0.9 [c] | | 28.9 ± 2.1 | | 14.6 ± 1.2 | |
| BIRM (10 μL/mL) | 67.93 ± 2.1 | +20.5% | 19.5 ± 2.4 | −32.5% | 12.5 ± 0.28 | −15% |
| BIRM (25 μL/mL) | 75.46 ± 2.2 | +33.8% | 13.1 ± 2.9 | −54.6% | 11.39 ± 0.29 | −22% |

[a] Flow cytometric cell-cycle fractionation analysis was performed in PC-3ML cells treated with BIRM for 24 h. Distributions of cells in various cell-cycle-phases were calculated from the DNA content of propidium iodide labeled cells using MODFIT program.
[b] Percent difference was calculated as ((% of cells in respective phase of untreated sample − % of cells in respective phase in BIRM treated samples) ÷ (% of cells in respective phase in untreated control) × 100)).
[c] Values are Mean and ± S.E. of three independent experiments. Similar results were obtained when other cells line (LNCaP) was exposed to BIRM and analyzed for cell-cycle phase fractionation.

This finding is novel because most of the plant-derived compounds, applicable to cancer therapy, interfere with either tubulin polymerization (e.g. vinblastin and vincristine) or depolymerization (paclitaxel), by inhibiting topoisomerase I activity (e.g. irinotecan, topotecan, 9-aminocamptothecin and 9-nitrocamptothecin) (Dennis et al., (2000) The Oncologist 5:185-198) or topoisomerase II activity all leading to cell cycle arrest in G2/M phase (e.g. paclitaxel, etopside and teniposide) (Pienta et al., (1996) Urology 48:164-170). Apoptotic cell death may be one of the mechanisms of BIRM-induced cytotoxicity. BIRM induced apoptosis in at least three CaP cell lines (FIG. 3). Furthermore, induction of apoptosis in BIRM treated CaP cells was coincident with activation of cell-death caspases (FIG. 4). In addition to its cytotoxic effects, BIRM appears to be a potent inhibitor of metastasis. Although, the mechanism by which it may inhibit metastasis is unknown at present, the present invention indicates that BIRM is a potent inhibitor of HAase, a class of matrix-degrading enzymes whose levels have been shown to correlate with prostate cancer progression. Lokeshwar et al., (1996) Cancer Res 56:651-657; Block et al., (2001) J Biol Chem 276: 11922-11932.) Given its effect on tumor growth and metastasis and no systemic toxicity, inclusion of BIRM, as an adjuvant to standard therapy has potential to reduce/halt disease progression.

In one aspect of the present invention, BIRM shows cytotoxic activity against both the androgen-dependent and androgen-independent CaP cells in vitro. BIRM reduces tumor incidence, delays tumor growth and causes a significant reduction of metastasis in an experimental model of late stage CaP. In another aspect of the present invention, continuous administration of BIRM did not show systemic toxicity in vivo, in the rat model.

EXAMPLE 13

Tumor generation and BIRM administration. This experiment was performed according to the University of Miami Animal Use and Care committee approved protocol and as stipulated in the NIH guide to the humane care and use of laboratory animals. A suspension ($1\times10^5$ cells, 0.5 ml) of growing EGFP-MAT Lylu cells was implanted in a subcutaneous site on the dorsal flank of adult, male Copenhagen rats (Harlan Sprague Dawley, Indianapolis, Ind.) under mild anesthesia. (Lokeshwar et al., (2002) J. Cancer 98:297-309.) Rats were housed in a room with 12 hour light and dark cycles, and provided ad libitum food and water supply throughout the experiment. Following implantation, the rats were randomly divided into 2 groups of 6 animals each to receive 1 ml of either distilled water (vehicle control, Group 1) or BIRM (Group 2) using a 3" stainless-steel intubation canula from day 1 of tumor implantation and continued daily for 30 days. Tumor growth was examined by palpating the skin around the site of injection. After the tumors became palpable (~day 5), tumor volumes were measured three times a week, with calipers and volume was approximated to an ellipsoid (length×width×0.524). Animals were euthanized when tumor volume was ≃10 cc or the tumor became significantly necrotic. At necropsy, lungs were collected and observed under a Nikon Stereo microscope with fluorescence attachment (SMZ 1500) to examine the presence of fluorescent metastatic tumor foci.

Statistical Analysis: Triplicate samples were assayed in all in vitro experiments. Statistical analysis was performed using parametric and non-parametric student t-tests.

EXAMPLE 14

BIRM inhibits cell proliferation in CaP cells. BIRM inhibited cell proliferation in all the CaP cell lines tested in a dose dependent manner (FIG. 1). The 50% growth inhibition dose ($IC_{50}$) of BIRM was 8 μl/mL (i.e., 0.8% v/v). Furthermore, the inhibitory activity of BIRM was comparable among all CaP cell lines, regardless of their androgen sensitivity [LNCaP and VcaP (androgen sensitive cells) versus PC-3ML and DU-145 (androgen resistant cells)]. Similar results were obtained by cell counting and Trypan blue exclusion assays. The results presented in FIG. 1 and similar observation from other assays suggested that BIRM-induced inhibition of cell proliferation leads to either cell death (cytotoxicity) or arrest of cell proliferation (cytostasis). To distinguish between these mechanisms, we investigated colony-forming efficiency of CaP cells treated with BIRM. Clonogenic assay revealed a dose-dependent inhibition of colony formation in BIRM treated CaP cells. Neither cell colonies nor cell clusters were observed in cultures exposed to BIRM≧10 μL/mL, for 24 h (FIG. 2A). The $IC_{50}$ of BIRM for inhibiting clonogenic survival is also 8 μL/mL, same as that obtained in the $^3$H-thymidine assay (FIG. 2B).

EXAMPLE 15

BIRM causes cell-cycle arrest in CaP cells. As shown in Table 1, the proportion of cells in $G_0/G_1$ phase increased significantly from 56.4±0.9% in control to 75.5±2.2% in cultures treated with BIRM (25 μl/ml BIRM). The increase in the $G_0/G_1$ phase fraction in the BIRM treated cells was contrasted with decrease in S-phase fractions. The S-phase fraction in BIRM treated sample was 13.1±2.9% compared to 28.9±2.1% in the control. A small decrease of 15% to 22% in $G_2/M$ fraction was also observed in BIRM treated cells.

EXAMPLE 16

BIRM induces apoptosis in CaP cells. A significant difference in the levels of free-nucleosomes in BIRM treated cells within 4 h of treatment was not observed, however, 24 h treatment revealed a 2-3-fold increase in the intracellular levels of free nucleosomes in a dose-dependent manner (FIG. 3).

EXAMPLE 17

Activation of cell death-associated caspases. As shown in FIG. 4, activities of one or more of the caspase-2, 3, 7, 8, 9 and 10 was increased significantly in BIRM treated cells as compared to control. A 50% increase over the activity found in control samples was observed at 0.5% BIRM, following an 18 h or longer incubation.

EXAMPLE 18

BIRM inhibits tumor growth and metastasis. As shown in FIG. 5, following tumor implant, oral administration of BIRM to rats resulted in slow tumor growth. While tumor incidence was 100% in the control group, only 4 out of 6 (67%) animals in BIRM-treated group developed tumors. Tumor growth rate estimated using a non-linear regression analysis of tumor volumes over time, for each animal, confirmed decreased growth rate in the BIRM treated animals. The time taken by tumors to reach 1 CC was 18.6 days±1.3 days (control) and 25.7±2.6 days (mean±SE from 4 animals) in BIRM treated group, respectively. A 38% delay was observed in BIRM treated group when compared to that of the control group. The difference in the growth rate between control and the BIRM treated groups was statistically significant (Unpaired t test: $p=0.03$; $t=2.773$, $df=6.95\%$ CI: 0.835 to 13.36). Tumor foci identified by fluorescence imaging of the lungs at necropsy revealed that only 1 out of 6 animals in the BIRM treated group had metastatic lung foci, whereas, 5 out of 6 animals in the control group had tumor metastasis to lungs. Furthermore, the tumor foci in the lung of BIRM-treated animal were significantly smaller than those in control group (FIGS. 6A, B). These results indicate that ingredients in BIRM delay/block spontaneous lung metastasis.

EXAMPLE 19

Figure 7:
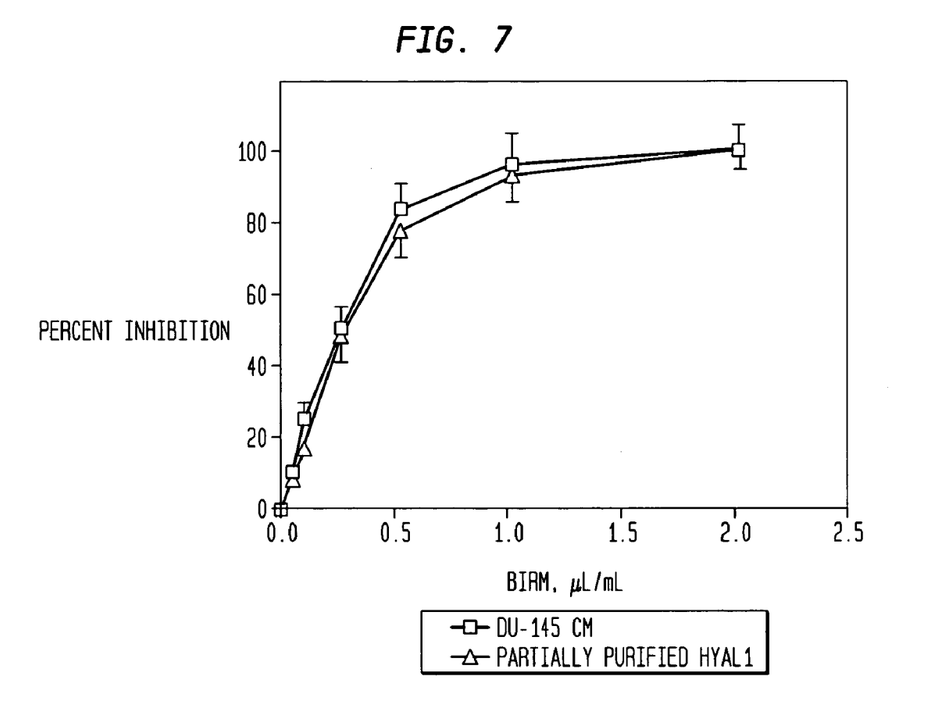
FIG. 7. BIRM inhibits tumor-derived HAase: Effect of BIRM on the HAase activity present in DU-145 cell conditioned medium and partially purified preparation of HYAL1 was carried out using the HAase ELISA-like assay, as described in "Materials and Methods". Data shown are from a typical experiment. Similar results were obtained in three other experiments using LNCaP cells.

BIRM inhibits the activity of HYAL1 type Haase. Investigation of inhibition of MMP activity by BIRM using a $^3$H-labeled-collagen degradation assay (Lokeshwar et al., (1993) Cancer Res 53:4493-4498) showed no changes in MMP activity following BIRM treatment. The inhibitory effect of BIRM on the activity of HYAL1 type Haase was examined. Previously it was shown that HYAL1 is the major HAase expressed in cancers of the prostate and bladder. (Block et al., (2001) J Biol Chem 276:11922-11932; Lokeshwar et al., (1999) Cancer Res 59:4464-4470.) Furthermore, invasive tumor cells express high levels of HYAL1. (Block et al., (2001) J Biol Chem 276:11922-11932; Lokeshwar et al., (1999) Cancer Res 59:4464-4470; Smith and Millis (2001) Cancer Pract 9:253-255.) As shown in FIG. 7, BIRM is a potent inhibitor of HAase activity. BIRM inhibited the HAase activity present in the culture-conditioned medium of DU-145 cells (a good source of HYAL-1 [22] (Lokeshwar et al., (1999) Cancer Res 59:4464-4470)) and the activity of partially purified HYAL1, in a dose-dependent manner ($IC_{50}=0.25$ μL/mL).

EXAMPLE 20

Figure 8:
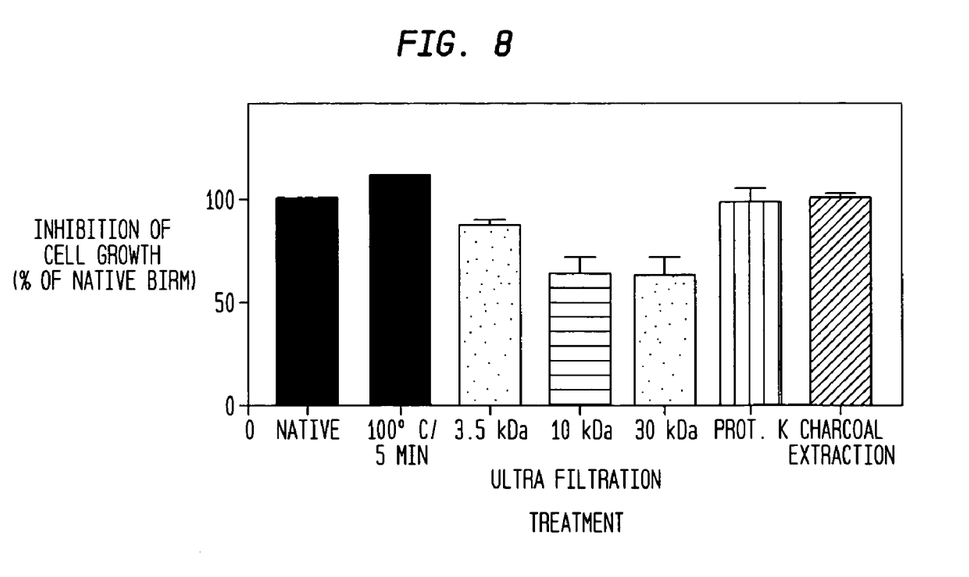
FIG. 8. Cytotoxicity of modified BIRM as assayed by MTT assay and compared with unmodified BIRM: BIRM solution was treated with proteinases (Proteinase K), heated for 5 min in a boiling water-bath or subjected to Ultra filtration as described in "Materials and Methods". Following treatment, untreated and treated BIRM solutions were tested for cytotoxic activity in PC3-ML cells by MTT assay, as described in "Materials and Methods". Vertical bars represent Mean±SEM, from four independent assays.
Figure 9:
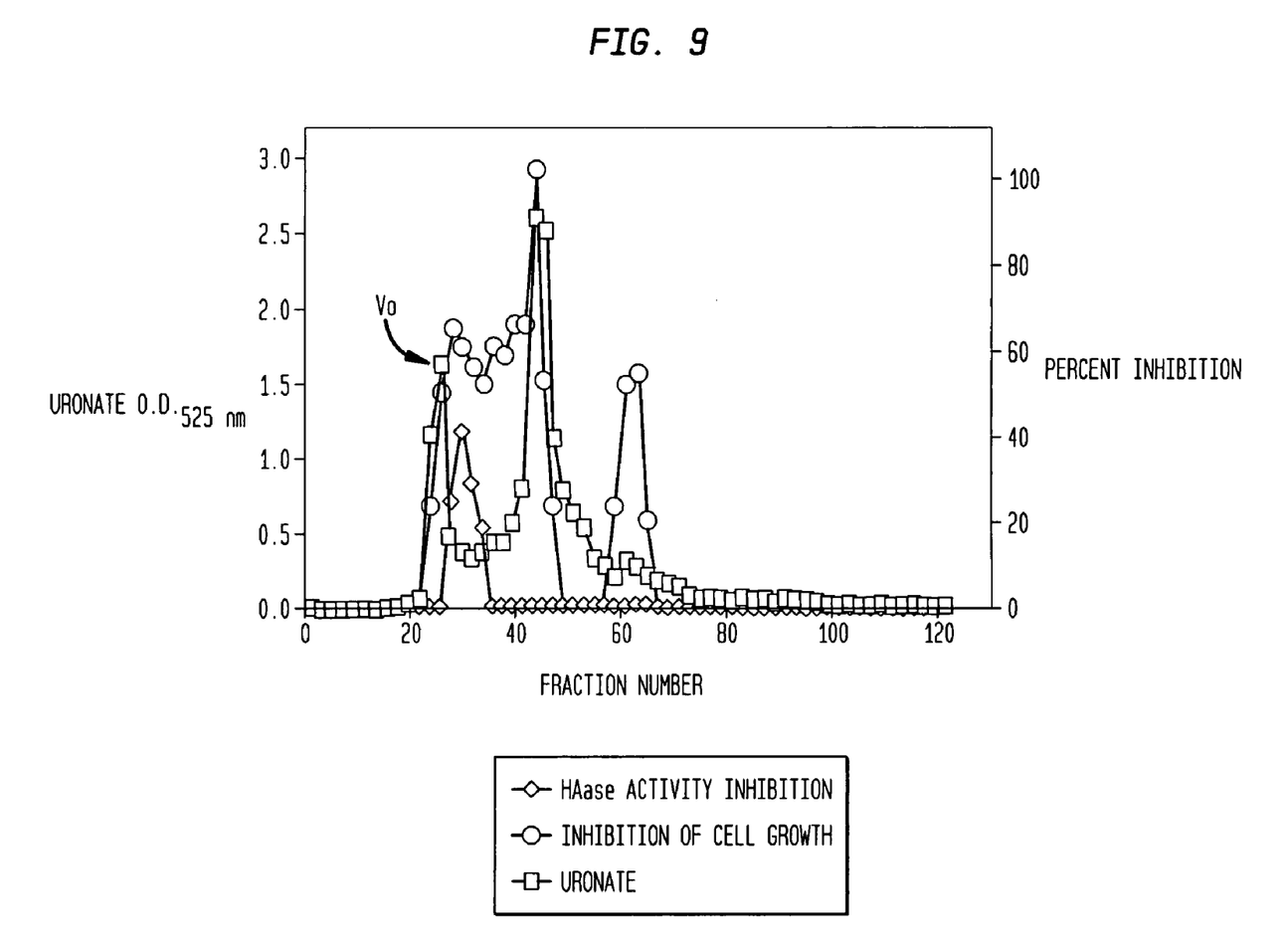
FIG. 9. Fractionation of anti-neoplastic ingredients present in BIRM by gel filtration chromatography: Five milliliter of clarified BIRM was fractionated on a Sephadex G-50 column. The column fractions were assayed for protein. ($A_{280\ nm}$), uronate concentration (Bitter and Muir assay), HAase activity (HAase activity ELISA) and cytotoxicity (MTT assay). A single protein peak was detected in fraction #20, which had neither cytotoxic activity nor HAase inhibitory activity.

Characterization of active ingredients in BIRM solution. BIRM retained its full cytotoxic activity after boiling for 5 min or digestion with proteinase K; indicating reactive species present in BIRM most likely are heat stable, proteinase resistant compounds. Similarly, charcoal-dextran extraction also did not result in any loss of the cytotoxic activity associated with BIRM, suggesting that the active species present in BIRM is not a lipid-soluble compound such as alkaloid, or steroid. Ultra filtration through molecular sieve membranes showed no loss of cytotoxic activity upon filtration through a 3.5 kDa membrane barrier. A 40% loss in activity was observed after Mr~10 kDa and Mr~30 kDa membrane Ultra filtration (FIG. 8). These results indicate that BIRM contains at least 2 molecular mass $\geq 30,000$, with cytotoxic activity against CaP cells. Possibility of carbohydrate derivatives associated with growth-inhibitory activity was scrutinized using the Bitter and Muir modified carbazole assay, to measure D-glucuronic acid (i.e., uronate) containing glycosaminoglycans and proteoglycans. (Mickey et al., (1980) Characterization of a human prostate adenocarcinoma cell line (DU 145) as a monolayer culture and as a solid tumor in athymic mice. (Prog Clin Biol Res 37:67-84.) Results show that BIRM is rich in uronate containing carbohydrates (19.5 mg/mL). Gel filtration chromatography on a Sephadex G-50 column also showed 2 active fractions at fraction No. 28 and 42 (FIG. 9).

EXAMPLE 21

Chemical and NMR analysis of an active ingredient in BIRM solution. Chemical analysis of an active ingredient in BIRM indicated that it had the following composition: % C, 40.84; % H, 5.64; % N, 0.55; % P, 0.31; % S, 0.85; % O, 38.25. NMR analysis of an active ingredient of BIRM confirmed the same composition.

EXAMPLE 22

Volunteer—Male, 63 years old, Equadorian citizen. The patient was diagnosed with prostatic adenocarcinoma in late November 1999. His PSA (prostrate specific antigen) was 9 ng/ml and he was treated for 6 months by androgen ablation using Zoladex and Casodex.

In May 1996, the patient underwent radical prostatectomy and bilateral lymph node dissection when metastasis was detected. Pathological evaluation of the excised tissue confirmed a Gleason score of 9 (confirming prostate cancer), severe androgen deprivation around the gland, and metastatic cancer in 5 lymph nodes. The patient continued Zoladex and Casodex treatment and PSA levels remained below 1.

When the patient discontinued hormone therapy approximately one year later, PSA levels rose to 9.4 but decreased slightly when the patient began Zoladex treatment only.

Beginning in May 1999, MRI bone scans revealed reactive bone formations consistent with metastasis in the right iliac wing and thoracic vertebral body. Also in May 1999, the patient began treatment with an oral form of BIRM at 4 mL/day.

In January 2000, bone scans detected additional evidence of metastases in the retroperitoneal and right internal iliac lymph nodes, an additional area on the thoracic spine, and diffuses marrow infiltration. The MRI results generally indicated widespread osseous metastases. Also at this time, however, the patient surprised doctors by stating that his pain had decreased significantly. In February 2000, the patient underwent thoracolumbosacral spine palliative radiation therapy. Two months after the treatment the patient again reported that his original pain was gone.

The patient experienced no new problems as of September 2000. Soon after February 2001, the patient discontinued Zoladex treatment and began taking DES. In March 2001 tests revealed increased disease of the cervicothoracic spine, left shoulder, and right iliac bone. When his pain increased in September 2001, he began a six cycle treatment of chemotherapy including Taxol.

As of March 2002, the patient's PSA levels remained increased (PSA 92 on Mar. 5, 2002) but CT scans showed no indication of visceral disease or retroperitoneal adenopathy, although there was some sclerosis in the right iliac bone.

The patient continued BIRM treatment for four years. After beginning BIRM treatment, the patient experienced decreased pain and fewer metastases.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All publications cited in the specification are indicative of the level of skill of those skilled in the art to which this invention pertains. All these publications are herein incorporated by reference to the same extent as if each individual publication were specifically and individually indicated to be incorporated by reference.

The invention claimed is:

1. A method of treating a mammal diagnosed with prostate cancer or at risk of developing prostate cancer, comprising administering to said mammal in need thereof a composition comprising a purified extract of the Amazonian variation of *Solanaceae Dulcamara* root, wherein said extract comprise an effective amount of Biological Immune Response Modifier comprising at least one uronate carbohydrate, at least one bio-organic mineral component selected from the group consisting of calcium, magnesium, aluminum, iron, manganese, silicon, zinc, and mixtures thereof, and wherein the composition has a density of at least 1.088.

2. The method of claim 1, wherein the composition is administered parenterally.

3. The method of claim 1, wherein the composition is administered orally.

4. The method of claim 3, wherein the composition is in the form of a tablet.

5. The method of claim 3, wherein the composition is in the form of a capsule.

6. The method of claim 3, wherein the composition is in the form of an emulsion, solution or suspension.

7. The method of claim 3, wherein the composition is administered buccally.

8. The method of claim 1, wherein the effective amount is about 0.1 µl/kg/day to about 100 µl/kg/day.

9. The method of claim 1, wherein the effective amount is about 1 µl/kg/day to about 20 µl/kg/day.

10. The method of claim 1, wherein the composition further comprises a pharmaceutically acceptable carrier.

11. The method of claim 1, wherein the mammal is a human.

12. The method of claim 1, wherein the mammal is at risk of developing prostate cancer.

13. The method of claim 1, further comprising administering to the mammal at least one other chemotherapeutic agent.

14. The method of claim 1, wherein the Biological Immune Response Modifier is prepared by a process comprising:
   a) harvesting root samples from the Ecuadorian plant *Solanaceae Dulcamara;*
   b) stabilizing the root samples;
   c) drying the root samples;
   d) modifying the root samples via oxidative reduction; and
   e) isolating a plant extract from the root samples, wherein the plant extract comprises Biological Immune Response Modifier.

15. The method of claim 14, wherein said stabilizing comprises heating the root samples at a temperature of about 20° C. to about 180° C.

16. The method of claim 15, wherein said heating is conducted at a temperature of about 79° C. to about 110° C.

17. The method of claim 15, wherein said stabilizing further comprises contacting the root samples with a solvent.

18. The method of claim 14, wherein said stabilizing comprises exposing the root samples to ultraviolet rays and ultrasound.

19. The method of claim 14, wherein said stabilizing comprises drying the root samples.

20. The method of claim 14, wherein said stabilizing comprises drying the root samples in an oven.

21. The method of claim 20, wherein the oven is selected from a group of ovens consisting of ventilation-type ovens, infrared ovens, and ovens in which pressure can be varied.

22. The method of claim 14, wherein said stabilizing comprises drying the root samples by solar drying.

23. The method of claim 14, wherein said stabilizing comprises autoclaving the root samples in the presence of a solvent.

24. The method of claim 14, wherein said modifying comprises reductive fermentation.

25. The method of claim 24, wherein said reductive fermentation comprises:
   a) adding the root samples to a fermenter;
   b) allowing fermentation to proceed under controlled amounts of oxygen for about 14 hours at about 70° C.;
   c) adding enzymes; and
   d) allowing fermentation to proceed under controlled amounts of oxygen for about 4 hours.

26. The method of claim 25, wherein said isolating comprises percolation.

27. The method of claim 1, wherein the Biological Immune Response Modifier contains at least 4 active species.

28. The method of claim 27, wherein at least two of the active species having cytotoxic activity.

29. The method of claim 28, wherein the Biological Immune Response Modifier contains three cytotoxic active species.

30. The method of claim 27, wherein the active species include at least one species with hyaluronidase inhibitory activity.

31. The method of claim 1, wherein the Biological Immune Response Modifier comprises oligomonosaccharides, nucleotides and wherein the oligomonosacharides comprise from about 14% to about 16% by weight.

32. The method of claim 31, wherein the oligomonosaccharides, and are selected from the group consisting of glucose, fructose, 1-ketose, 1-beta-furanosyl fructose, and mixtures thereof.

33. The method of claim 1, wherein the Biological Immune Response Modifier comprises an oligomonosaccharide having a condensed molecular formula of $(C_7H_9O_6, Mg, Ca)_n$, wherein $n \geq 1$.

34. The method of claim 17 or 23 wherein the solvent is selected from the group consisting of water, alcohol vapors or mixtures thereof.

35. The method of claim 34, wherein said isolating comprises evaporating solvents from a mixture containing the plant extract.

36. A method of treating a mammal suffering from prostate cancer or at risk of developing prostate cancer comprising orally administering to the mammal in need thereof a therapeutically effective amount of a composition obtained from the Ecuadorian plant *Solanaceae Dulcamara* said composition comprising a purified extract of *Solanaceae Dulcamara* root, wherein said extract comprise an effective amount of Biological Immune Response Modifier comprising at least one oligomonosaccharide having a condensed molecular formula of $(C_7H_9O_6, Mg, Ca)_n$, and a molecular weight of about $(251.38)_n$, wherein $n \geq 1$.

37. The method of claim 36, wherein the Biological Immune Response Modifier has a pH of about 7.1, and at least about 14% sugars.

38. The method of claim 37, wherein the Biological Immune Response Modifier comprises at least two bio-organic mineral selected from the group consisting of aluminum, iron, calcium, magnesium, manganese, silicon, zinc, and mixtures thereof.

* * * * *